United States Patent
Laird (10) Patent No.: US 6,276,661 B1
(45) Date of Patent: Aug. 21, 2001

(54) PRESSURE ACTUATED INTRODUCER VALVE

(75) Inventor: Robert James Laird, Richmond, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 08/744,659

(22) Filed: Nov. 6, 1996

(51) Int. Cl.[7] .................... F16K 7/07; F16K 31/126; A61M 5/178; A61M 25/01
(52) U.S. Cl. .................... 251/61.1; 137/317; 251/5; 604/167.02; 604/167.03; 604/256; 604/264
(58) Field of Search .................... 251/61.1, 5; 604/9, 604/212, 236, 245, 246, 280, 264, 335, 167.01, 167.02, 167.03, 167.06, 256; 137/317

(56) References Cited

U.S. PATENT DOCUMENTS

| | | | |
|---|---|---|---|
| 2,945,665 | * 7/1960 | Regan et al. | 251/5 |
| 2,984,448 | * 5/1961 | Koplin | 251/61.1 |
| 3,703,140 | * 11/1972 | Gutheim | 251/61.1 |
| 3,737,139 | * 6/1973 | Watts | 251/5 |
| 3,936,028 | * 2/1976 | Norton et al. | 251/61.1 |
| 4,135,698 | * 1/1979 | Thate | 251/61.1 |
| 4,206,929 | * 6/1980 | Bruce | 251/5 |
| 4,345,735 | * 8/1982 | Regan | 251/5 |
| 4,465,258 | * 8/1984 | Weingarten | 251/61.1 |
| 4,662,598 | * 5/1987 | Weingarten | 251/5 |
| 4,705,518 | 11/1987 | Baker et al. | 623/14 |
| 4,706,738 | * 11/1987 | Heimbrodt et al. | 251/61.1 |
| 4,850,953 | 7/1989 | Haber et al. | 600/32 |
| 5,071,411 | * 12/1991 | Hillstead | 251/5 |
| 5,127,626 | 7/1992 | Hilal et al. | 251/149.1 |
| 5,158,553 | 10/1992 | Berry et al. | 604/248 |
| 5,161,773 | * 11/1992 | Tower | 251/5 |
| 5,197,955 | 3/1993 | Stephens et al. | 604/167 |
| 5,209,737 | 5/1993 | Ritchart et al. | 604/167 |
| 5,211,370 | 5/1993 | Powers | 251/4 |
| 5,211,683 | 5/1993 | Maginot | 128/898 |
| 5,279,597 | 1/1994 | Dassa et al. | 604/283 |
| 5,300,047 | 4/1994 | Beurrier | 604/264 |
| 5,304,220 | 4/1994 | Maginot | 623/1 |
| 5,338,313 | 8/1994 | Mollenauer et al. | 604/249 |
| 5,350,364 | 9/1994 | Stephens et al. | 604/167 |
| 5,360,417 | * 11/1994 | Gravener et al. | 251/5 |
| 5,366,478 | 11/1994 | Brinkerhoff et al. | 660/213 |
| 5,456,712 | 10/1995 | Maginot | 623/1 |

FOREIGN PATENT DOCUMENTS

WO98/17341 4/1998 (WO).

* cited by examiner

Primary Examiner—George L. Walton (57) ABSTRACT

The invention provides highly adaptable valves for providing hemostasis about minimally invasive surgical implements such as guidewires and endovascular prosthetic delivery catheters. The valves generally comprise an elastomeric sealing body which will maintain hemostasis by contacting a surgical implement traversing the valve over a very small contact area. Preferably, the orifice is formed in a thin membrane which extends radially inward from a torroidal balloon having a relatively rigid outer rim and a flexible inner portion. When a vacuum is applied within such a balloon, the flexible inner portion pulls the membrane radially outward to expand the orifice diameter. A positive pressure can be applied within the torroidal balloon so that the balloon expands radially inward to block access through the valve.

22 Claims, 6 Drawing Sheets

PRESSURE ACTUATED INTRODUCER VALVE

BACKGROUND OF THE INVENTION

1. Field of the Invention

The present invention generally relates to introducer valves for surgical procedures, and more particularly, provides a pressure actuated valve which can maintain hemostasis around surgical instruments having a wide variety of cross-sectional diameters.

Introducer valves are used in a wide variety of minimally invasive and conventional surgical procedures. For example, laparoscopic and arthroscopic surgical procedures are often performed through trocar assemblies which include introducer valves. After a rigid trocar tube is inserted to provide access to a body cavity, surgical implements or tools are inserted into and withdrawn from a sealing valve located at a proximal end of the trocar tube. The introducer valve generally prevents fluid from inadvertently leaving or entering the body cavity through the trocar tube.

Current introducer valves generally fall into two basic categories: passive and active. A passive valve generally relies on the deformation of a resilient sealing body by the implement inserted through the valve to form the desired fluid tight seal. Active surgical valves include a mechanism that moves a sealing body into contact with the traversing implement.

A wide variety of passive and active surgical valve structures have been proposed. While these structures have met with varying degrees of success and acceptance, they generally have suffered from a common disadvantage: sealing bodies (whether passive or active) which seal effectively over a wide variety of cross-sectional diameters tend to impose substantial frictional forces on at least some sizes of traversing implements.

In fact, despite the wide variety of introducer valves which have been proposed, the use of simple fixed o-rings or grommets remains common. While these simple sealing devices accommodate only a very narrow range of surgical implement diameters, the seals provided within that range are reliable and the friction forces are light.

Recently, endovascular surgical procedures have been developed which place even more stringent demands on introducer valves. Of specific interest to the present invention, the endovascular placement of vascular stents, grafts, stent-grafts, and other endoluminal prostheses for the treatment of abdominal aortic aneurysms and other vascular diseases has been proposed. Such endovascular prosthetic placement will generally require the use of relatively large prosthetic deployment catheters, typically having an outer diameter in the range from about 4 mm to 10 mm. These large deployment catheters will require correspondingly large introducer sheaths, typically having an internal lumen diameter which is at least slightly larger than the outer diameter of the deployment catheter. These large sheaths will generally provide direct access to the major arteries of the vascular system, and will thus be subjected to relatively high blood flow rates and pressures. The target sites for deployment of these protheses, however, will often be at a considerable distance from the vascular access sites, and intravascular maneuvering to reach the target site is often performed with much smaller diameter implements. Work in connection with the present invention has shown that maintaining hemostasis while accessing the target site and deploying the endovascular prostheses can be problematic.

An exemplary endovascular procedure will involve deployment of endovascular prostheses to isolate abdominal aortic aneurysms. Access will generally be provided either through the femoral artery and beyond the hypogastric branch and the aorto iliac junction, or down through the subclavian artery, through the aortic arch, and into the thoracic aorta. In either case, the path will generally first be negotiated by flexible intravascular guidewires having very small diameters. Ideally, the hemostasis valve should allow delicate maneuvering of both the very small vascular guidewires and the large delivery catheters, preferably while maintaining effective hemostasis throughout the positioning and deployment procedure.

For these reasons, it would be desirable to provide improved hemostatic valves for use in endovascular, laparoscopic, and other surgical procedures. Such valves should preferably seal over a wide range of surgical implement diameters, preferably without imposing the high frictional forces of known vascular valves, regardless of the cross-sectional size of the surgical implement traversing the valve.

2. Description of the Background Art

U.S. Pat. No. 5,366,478, describes an endoscopic surgical sealing device. In one embodiment, the device comprises an uninflatable toroid which is used to seal a trocar. U.S. Pat. Nos. 5,350,364, and 5,197,955 describe a trocar assembly having a seal member that is generally of hourglass shape, defining converging and diverging sidewalls that form a constricted center bore portion therebetween. Various alternative means are described to either increase or decrease the inner diameter of the center bore portion of the seal member. U.S. Pat. No. 4,705,518, describes an artificial sphincter apparatus, operation of which is effected by a number of remote and proximate actuation means. U.S. Pat. No. 4,850,953, describes a gastrostomy valve provided with an expansible membrane or balloon which assumes a torroidal configuration to seal against the abdominal wall. U.S. Pat. No. 5,127,626, describes an apparatus for sealing around shafts or tubes of varying diameter. U.S. Pat. No. 5,158,553, describes a rotatably actuated constricting catheter valve. A trocar canula and catheter assembly which optionally includes an inflatable sealing bladder is described in U.S. Pat. No. 5,300,047.

An exemplary adjustable valve having a radially compressible sealing body is described in U.S. Pat. No. 5,338,313, while U.S. Pat. Nos. 5,209,737 and 5,279,597, are generally relevant.

SUMMARY OF THE INVENTION

The present invention provides highly adaptable valves which are particularly useful for providing hemostasis about minimally invasive surgical implements such as guidewires and endovascular prosthetic delivery catheters. The present valves generally comprise an elastomeric sealing body which will maintain hemostasis by contacting a surgical implement traversing the valve with a very small contact area. Preferably, this small contact area is provided by an orifice which is formed in a thin membrane that extends radially inward from a torroidal balloon. The balloon has a relatively rigid outer rim and a flexible inner portion. When a vacuum is applied within such a balloon, the flexible inner portion pulls the membrane radially outward to expand the orifice diameter. If complete blockage of the orifice is desired, a positive pressure can be applied within the torroidal balloon so that the balloon expands radially inward to block access through the valve. Alternatively, a positive pressure can be applied to seal more firmly around a small-diameter implement traversing the valve, and/or to temporarily hold the surgical implement immobilized. Hence, these valves provide both low friction manipulation of instruments (due to their small, o-ring like contact pattern) with an ability to provide effective hemostasis around surgical implements having widely varying cross-sectional diameters.

In a first aspect, the present invention provides a valve comprising a torroidal balloon having a substantially rigid outer rim and a flexible inner portion which define a torroidal space therebetween. An elastomeric membrane extends radially inward from the inner portion of the torroidal balloon to an orifice having a nominal diameter. A pressure varying system is in communication with the torroidal space. This pressure system is capable of providing a vacuum within the torroidal space so that the inner portion of the torroidal balloon distends the membrane to enlarge the orifice beyond the nominal diameter.

In many embodiments, the pressure system will further be capable of increasing pressure within the torroidal space so that the membrane or inner portion of the torroidal balloon occludes the orifice. The variability of the orifice can be enhanced by providing the outer rim of the balloon with a groove which is substantially aligned with the membrane.

In another aspect, the present invention provides a hemostasis valve comprising a substantially rigid valve body and an elastomeric sealing body. The rigid valve body has a passage which defines an axis, while the sealing body includes first and second walls which extend radially inward from the passage and axially toward each other. These walls support an orifice of the sealing body which has a nominal diameter when the sealing body is at rest. The walls and passage define a substantially sealed torroidal space therebetween. A pressure varying system is in communication with that torroidal space to draw a vacuum within the torroidal space and collapse the walls radially outward from the axis. As the walls collapse, they expand the orifice to an enlarged diameter. The pressure system is further capable of pressurizing the torroidal space with a valve-occluding closing pressure. This pressure expands the walls radially inward so that flow through the orifice is occluded.

In a particularly preferred embodiment, the pressure system comprises a three position actuation mechanism for selectively applying a valve closing pressure, the vacuum, and some particular pressure therebetween. Ideally, these three positions (and their corresponding pressures) are selected so that the valve is substantially closed, provides low friction manipulation and hemostasis around a guidewire, or provides low friction manipulation and hemostasis around a large endovascular prosthesis delivery catheter for the repair of an abdominal aortic aneurysms.

In another aspect, the present invention provides a hemostasis valve comprising a substantially rigid valve body having a passage which defines an axis. An elastomeric sealing body is within the passage of the valve body, the sealing body having an orifice which is alignable with the axis. An actuator is coupled to the sealing body to vary an effective size of the orifice. The actuator is selectably movable between first and second positions. When in the first position, the sealing body provides low-friction hemostasis about a first surgical implement with a first predetermined cross-section. When the actuator is in the second position, the sealing body provides low-friction hemostasis about a second surgical implement having a second cross-section which is larger than the first cross-section.

DETAILED DESCRIPTION OF THE SPECIFIC EMBODIMENTS

The valves of the present invention will have applications in a wide variety of medical procedures, including both minimally invasive and traditional surgical methods. These valves will find particularly advantageous use in laparoscopy, arthroscopy, endoscopy, and other minimally invasive surgical procedures to seal trocar and access catheters used to gain access to internal body therapy sites. The valves of the present invention may further find use in fields outside the area of medicine, and are especially well adapted for preventing flow around objects of various diameters without imposing large frictional forces on those objects. This invention will find its most immediate use, however, as an access valve disposed at the proximal end of a tubular sheath to provide access to the vascular system. Such access valves can provide hemostasis around a wide variety of vascular surgical tools and devices, from a small endovascular guidewire to a large tubular bifurcated prosthetic system, as might be used in therapy of an abdominal aortic aneurysm. An exemplary vascular access sheath structure is described in copending U.S. patent application Ser. No. 08/330,140, filed Oct. 24, 1994, while the use of such a large access sheath for aneurysm repair is described in U.S. patent application Ser. No. 08/475,200, filed Jun. 7, 1995, the full disclosures of both of which are hereby incorporated by reference.

Figure 1:
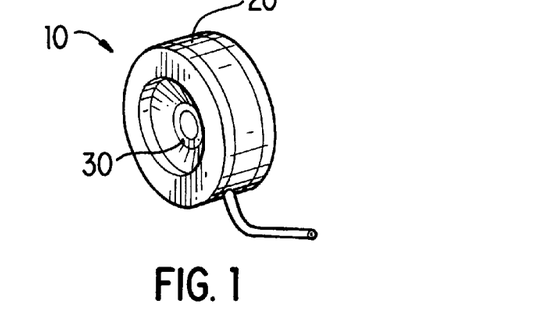
FIG. 1 is a perspective view of an introducer valve according to the principles of the present invention.
Figure 1A:
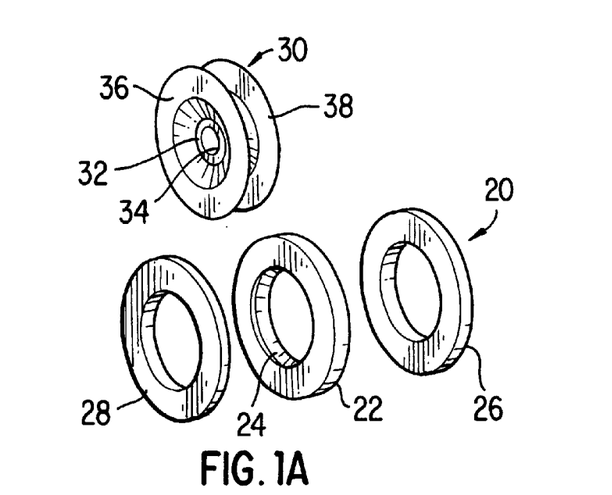
FIG. 1A is an exploded view of the components of the valve of FIG. 1.

Referring first to FIGS. 1 and 1A, an access valve 10 generally comprises a substantially rigid valve body 20 and an elastomeric sealing member 30. Valve body 20 comprises a body or disk 22 having a hole or passage extending therethrough, and a rim defining the passage or hole, and an internal groove 24. The passage or hole also defines an interior surface of disk 22. Endplates 26, 28 are disposed on opposite sides of disk 22.

Elastomeric body 30 generally comprises a thin, planar membrane 32 having an outer perimeter and an orifice 34. Fixed to membrane 32, and extending radially outward from the perimeter of membrane 32, in opposite directions relative to the plane of membrane 32 are two walls or webs 36, 38. Walls or webs 36, 38 have inner edges that are sealingly connected to each other at the perimeter of membrane 32, and extend from the perimeter of membrane 32 to circumferential attachment locations on the rim of body 20. Elastomeric sealing member 30 is generally positioned with membrane 32 aligned with the internal groove 24 of disk 22. Webs 36, 38 extend radially along the sides of the disk, and endplates 26, 28, which define the attachment locations, hold these webs in compression against the sides of the disk so that a torroidal or annular space 40 is defined between elastomeric sealing member 30 and the rigid valve body 20 (as can be seen in FIG. 1B).

The rigid valve body will generally comprise a substantially rigid material such as a metal, a polymer, or the like. The elastomeric sealing member will generally comprise a highly distensible material such as latex, silicone, or the like. In some embodiments, the endplates will be fastened to ring 22 by bolts, rivets, clamps, clips, or the like. Alternatively, the elastomeric sealing member may be adhesively bonded, molded into, ultrasonically welded, or the like. In some embodiments, it may be possible to form the elastomeric sealing member and the rigid valve body as a unit from a single material, and provide the differing properties for the valve body and sealing member by having different material thicknesses, treatments, or the like. Hence, a variety of specific production methods might be used.

Figure 1B:
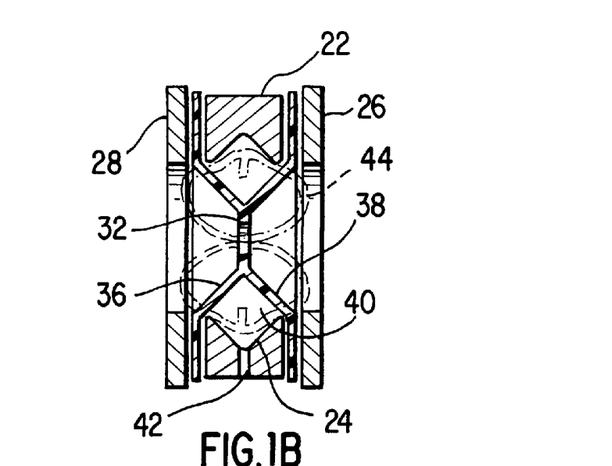
FIG. 1B is a cross-sectional illustration of the valve of FIG. 1, and shows the torroidal balloon in each of its three configurations.

The operation of the introducer valve 10 can be understood with reference to FIG. 1B. As described above, the webs 36, 38 of elastomeric sealing body 30 and the rigid valve body 20 define a torroidal space 40 therebetween. Lumen 42 is provided in the rigid valve body so that the pressure within torroidal space 40 can be selectively varied. When pressure within torroidal space 40 is increased, the elastomeric webs 36, 38 are distended, bulging radially inward to a closed configuration 44 (shown in phantom). Rigid valve body 20, and in particular disk 22, easily absorbs the pressure within torroidal space 40 without substantially bulging radially outward. Thus, the elastomeric sealing member and valve body effectively define a torroidal balloon having a substantially rigid outer rim. By increasing the pressure within that torroidal balloon, the inner portion is made to expand radially inward to close, and in some embodiments, seal the orifice of the valve entirely. Sealing may be provided by engaging opposed portions of the webs 36, 38 and/or membrane 34 adjacent orifice 32.

As is also shown in FIG. 1B, the pressure within torroidal space 40 may be reduced to increase the diameter of the orifice through the sealing member. By applying a vacuum relative to an ambient pressure surrounding the valve, that surrounding pressure collapses webs 36 and 38 radially outward toward the rigid valve body. As the webs move outward, they place the inner membrane 32 under tension, drawing the membrane radially outward substantially evenly along its circumference. This radial tension distends the membrane and increases the size of the orifice. When the vacuum is released and ambient pressure is again allowed into torroidal space 40, the webs of the elastomeric sealing member and the radially tensioned membrane 32 resiliently return to their original configuration, as shown in FIG. 1.

Figure 2:
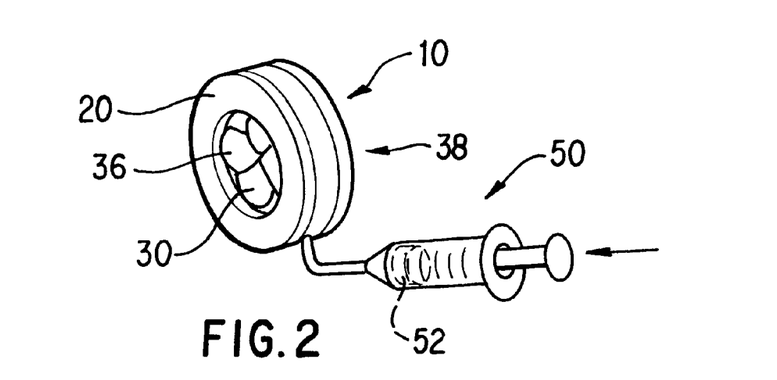
FIG. 2 is a schematic illustration of the valve of FIG. 1 with a positive pressure applied within the torroidal balloon so as to close the valve.
Figure 3:
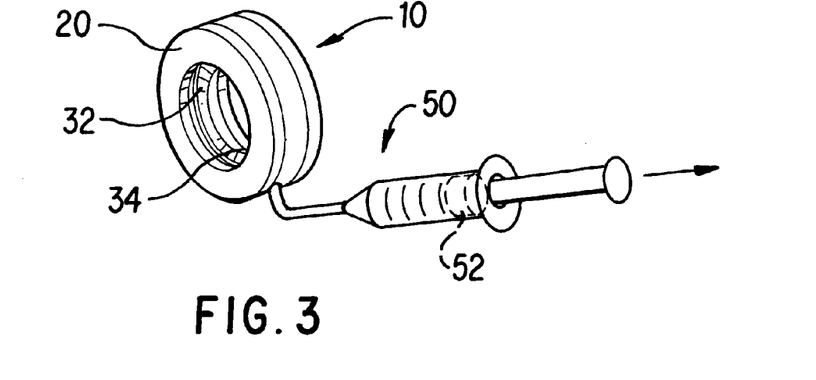
FIG. 3 is a schematic illustration of the valve of FIG. 1 in which a vacuum has been applied within the torroidal balloon so that the inner portion of the balloon collapses radially outward and distends the orifice.

Referring now to FIGS. 2 and 3, a simple pressure varying system 50 makes use of a positive displacement piston 52 to vary the effective size of the orifice of valve 10. Moving piston 52 in the direction indicated in FIG. 2 pressurizes a fluid within the torroidal space so that webs 36 and 38 resiliently expand to reduce the effective size of the open orifice. It will often be desirable to apply sufficient pressure with pressure system 50 so as to shut off any flow through the valve entirely. Advantageously, if some device traverses the valve when such pressure is applied, the bulging elastomeric member will seal with greater pressure and a large contact are around that traversing tool. Hence, such pressurization of the torroidal space can be used to fix the location of a guidewire or other minimally invasive surgical implement traversing valve 10.

Actuation of pressure system 50 also allows the application of a vacuum within the torroidal space so as to increase the effective open diameter of valve 10, as illustrated in FIG. 3. As described above, the ambient pressure acts upon the webs of the elastomeric member so that the torroidal space collapses radially outward, distending membrane 32 outward in all radial directions around the axis of the valve. To minimize the required actuation displacement of piston 52, it will often be desirable to fill the torroidal space with a liquid such as water. Alternatively, any other fluid may also be used, such as a saline solution, air, nitrogen, or the like.

The simple positive displacement system illustrated in FIGS. 2 and 3 may be replace with a wide variety of alternative pressure systems. In many embodiments, it will be advantageous to include a shut-off valve between the pressure system and the valve body, so that the pressure or vacuum within the torroidal space can be easily maintained. Often times, particularly when valve 10 is used in a surgical setting, the actuation pressure and/or vacuum may be supplied with standard pressurization and aspiration systems which are commonly available in the operating room. Alternatively, a dedicated pressure and vacuum system may be provided. In some embodiments, it may be possible to have the pressure regulated automatically depending on the size of the implement advancing towards the valve, using a sensor mounted proximally of the valve itself within an introducer system proximal housing.

Figure 4:
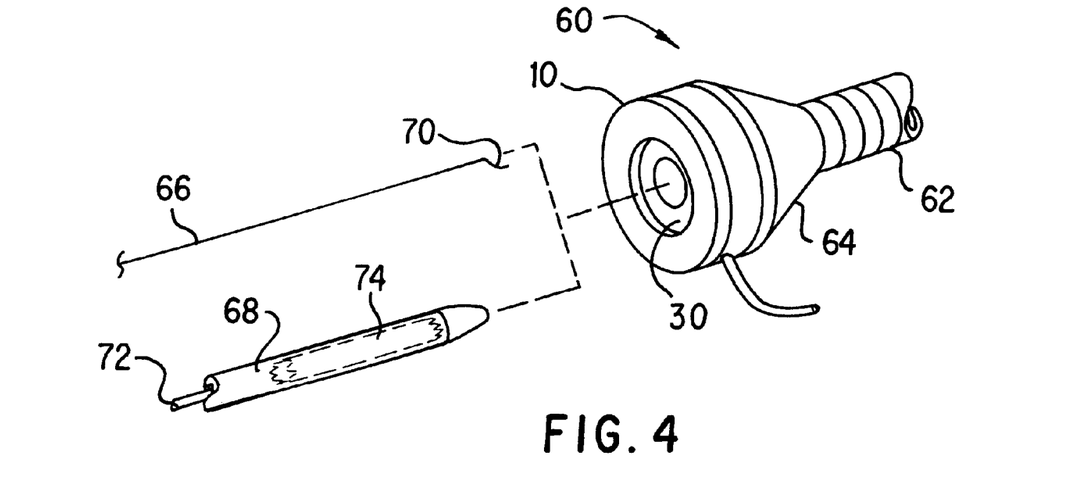
FIG. 4 schematically illustrates the use of the valve of FIG. 1 to provide hemostasis for a small diameter guidewire and a large introducer sheath during an endovascular prosthesis deployment procedure.

A particularly advantageous use of the valve of FIG. 1 is illustrated in FIG. 4. Valve 10 is here used within an introducer system 60, which also includes a flexible introducer sheath 62 and a proximal housing 64. A particularly advantageous introducer system is described in co-pending U.S. patent application Ser. No. 08/330,140, previously incorporated herein by reference.

The introducer system 60 will ideally be used to allow access for a guidewire 66 and an endovascular prosthesis delivery catheter 68. In some embodiments, elastomeric body 30 will be adapted so as to provide hemostasis around guidewire 66 when the pressure within the torroidal space is equal to ambient pressure, that is, when the orifice is at its nominal diameter. In such embodiments, the nominal diameter of the orifice of elastomeric sealing member 30 is generally slightly smaller than a cross-section of guidewire 66, so as to contact the guidewire with sufficient resilient force to provide hemostasis, but without imposing substantial frictional forces when the guidewire is moved axially or rotationally. This allows the guidewire to be maneuvered intravascularly using a bent distal tip 70, typically under the direction of fluoroscopy or some other medical imaging modality.

Preferably, the frictional forces imposed by the elastomeric sealing member on the guidewire will be less than the column strength of the guidewire so that the guidewire can be easily advanced distally through the valve. In some embodiments, an intermediate amount of positive pressure within the torroidal space may be required to provide sealing over a guidewire, in order to allow the orifice to also accept the larger implements required for a particular procedure.

Once guidewire 66 has been positioned across a target location of the vascular system, prosthetic delivery catheter 68 will often be introduced through valve 10, typically over the guidewire by passing a proximal end of the guidewire through a guidewire lumen 72. Prosthetic delivery catheter 68 will be significantly larger in diameter than the guidewire, typically being between about 4 and 10 mm in diameter. To accommodate this large diameter, and to maintain low-friction hemostasis, the orifice of elastomeric sealing member 30 is distended by decreasing the pressure within the torroidal space of the valve. The prosthetic delivery catheter is advanced over the guidewire 66 until a prosthesis 74 is located at the target location of the vascular system, as will generally be verified under fluoroscopy. The prosthesis will there be radially expanded, generally either resiliently (by withdrawing the outer catheter and maintaining the axial position of the prosthesis) or plastically (by inflating a balloon catheter or other expansion device within a prosthetic lumen). A particularly advantageous prosthetic delivery system was more fully described in co-pending U.S. patent application Ser. No. 08/475,200, previously incorporated by reference, while a preferred endovascular prosthetic structure was described in co-pending U.S. patent Application Ser. No. 08/615,697, filed Mar. 13, 1996, the full disclosure of which is herein incorporated by reference.

Advantageously, the contact between the elastomeric sealing member 30 and both the guidewire 66 and the prosthetic delivery catheter 68 comprises a narrow contact band surrounding the implement traversing the valve. Additionally, the orifice of the sealing member is disposed within a thin, flexible sheet. Both of these factors increase the maneuverability of both small and large implements through the valve, which is particularly important for accurate positioning and deployment of endoluminal prostheses, and for other minimally invasive therapies.

Figure 5A:
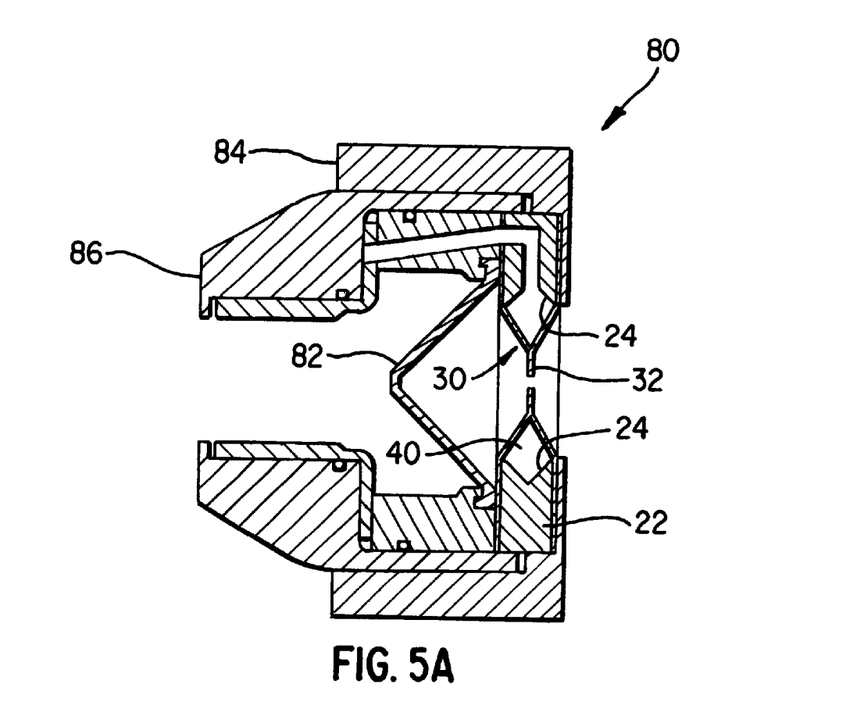
FIGS. 5A and 5B illustrate an alternative valve according to the principles of the present invention in which the valve body is provided with a positive displacement vacuum system, and in which a duckbill valve is provided to maintain hemostasis when no surgical implement traverses the valve.
Figure 5B:
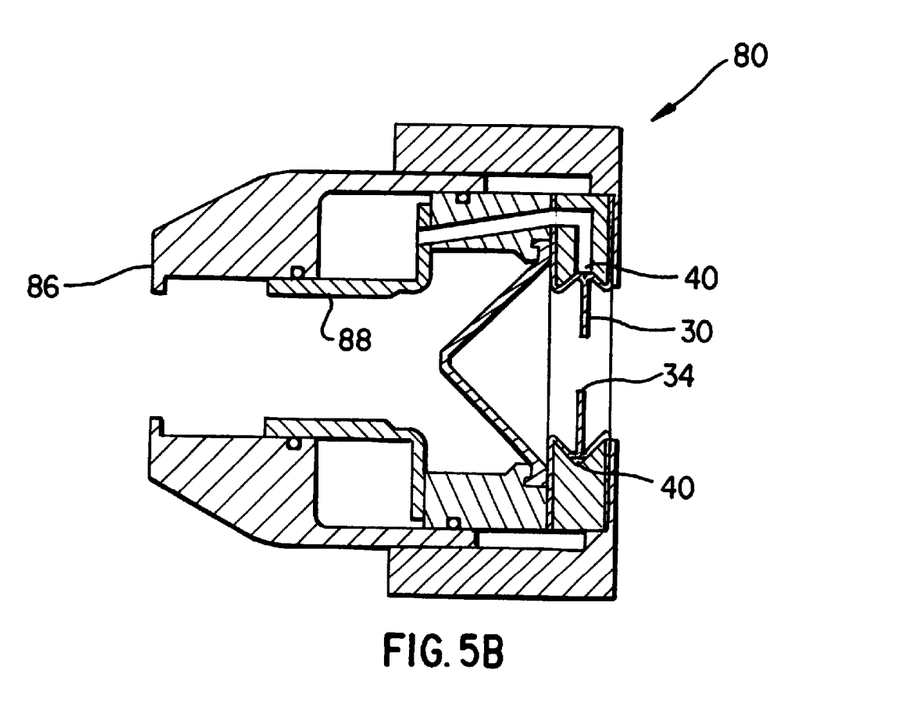

Referring now to FIGS. 5A and 5B, an alternative valve 80 includes both an elastomeric sealing member 30 and a duckbill valve 82 within valve body 84. Valve body 84 further includes an integral displacement mechanism 86 which, when moved relative to the remainder of valve body 84, varies the volume of a vacuum chamber 88. In this embodiment, the vacuum chamber is used to increase the diameter of orifice 34 from a nominal diameter, as shown in FIG. 5A, to an enlarged diameter, as shown in FIG. 5B. When no implement traverses the valve, hemostasis is provided by a simple duckbill 82.

Figure 6A:
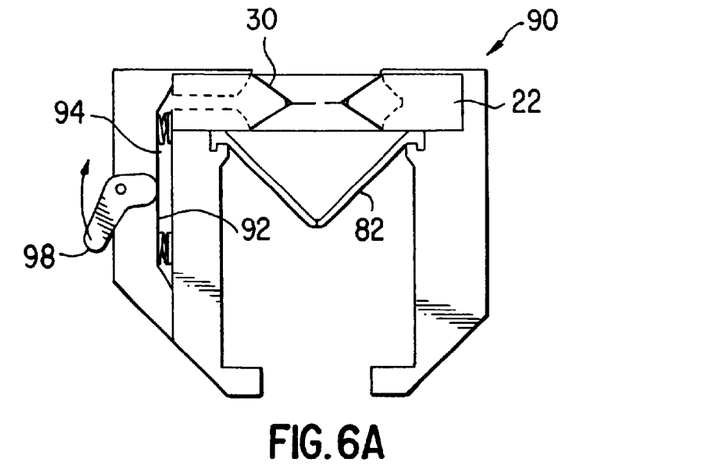
FIGS. 6A and 6B illustrate an alternative positive displacement vacuum system.
Figure 6B:
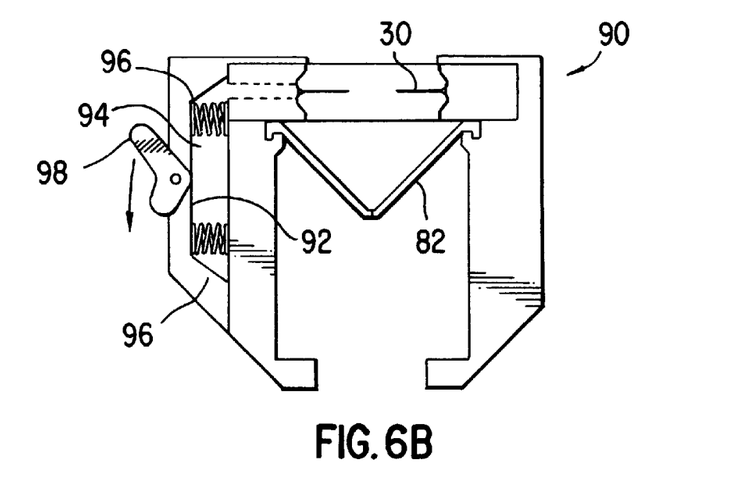

Referring now to FIGS. 6A and 6B, a biased diaphragm actuated valve 90 includes a diaphragm 92 which is sealed around a vacuum chamber 94, and which is biased to expand the vacuum chamber by springs 96. Actuation of a lever 98 varies the size of the vacuum chamber incrementally as shown, so that the elastomeric sealing member 30 varies between a first configuration having a relatively small orifice, as illustrated in FIG. 6A, and a relatively large orifice configuration, as illustrated in FIG. 6B. Once again, the small configuration is preferably sized to provide low friction hemostasis around a guidewire, while the large diameter configuration provides a similar low friction hemostasis around a large implement such as a prosthetic delivery catheter. Duckbill valve 82 will generally be disposed distally of elastomeric sealing body 30, so that minimally invasive surgical tools which are inserted through the valve will pass first through the elastomeric sealing member, and then through the duckbill valve 82 when advanced into the patient body.

Figure 7:
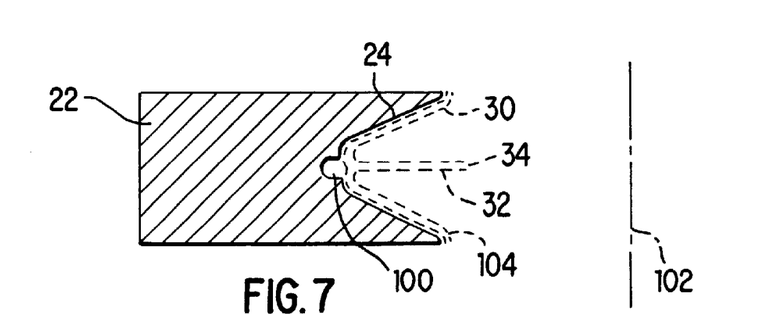
FIG. 7 is a cross-section of a valve body ring having a groove to enhance the variability of the valve orifice, and also having a vacuum channel to ensure that pressure is evenly distributed circumferentially about the valve.

Certain preferred features of ring disk 22, and a preferable interaction between the ring disk and the elastomeric sealing member, will be explained with reference to FIG. 7. As described above, the ring disk generally includes an internal groove 24 into which the elastomeric sealing member collapses radially outward when the pressure within the torroidal space is reduced. Preferably, ring disk 22 further includes a vacuum channel 100 to distribute the pressure within the torroidal space circumferentially. In the embodiment of FIG. 7, the elastomeric sealing member 30 collapses radially outward into groove 24, but does not impinge into vacuum channel 100 so as to block flow to the lumen to the vacuum chamber. This prevents the elastomeric sealing member from inadvertently sealing between the torroidal space and the pressure varying system.

Another feature which can be seen in FIG. 7 is that the orifice 34 through membrane 32 is preferably sized so that the orifice protrudes radially inward toward an axis 102 of the valve farther than any adjacent structure of the valve body or elastomeric sealing member, even when the orifice is in the large configuration. This ensures that the seal provided by the valve will rely primarily on a contact area between the orifice and the tool traversing the valve, rather than on an edge of the valve 104, or the like. This helps keep the contact area between the traversing tool and the valve to a minimum, thereby avoiding imposition of additional frictional forces.

Figure 8A:
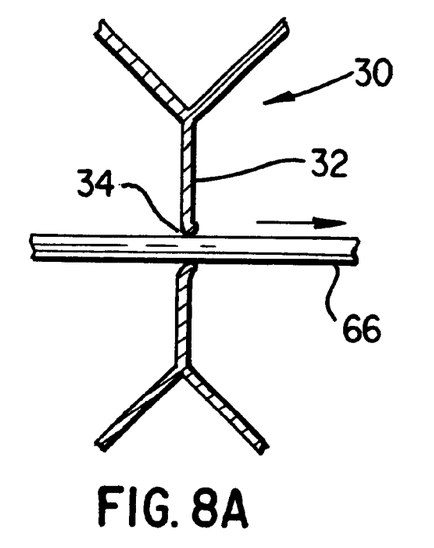
FIGS. 8A and 8B illustrate the relatively small contact sealing pattern the orifice of the valve of FIG. 1 against a small surgical implement such as a guidewire, and also against a large surgical implement such as an endovascular prosthesis delivery catheter.
Figure 8B:
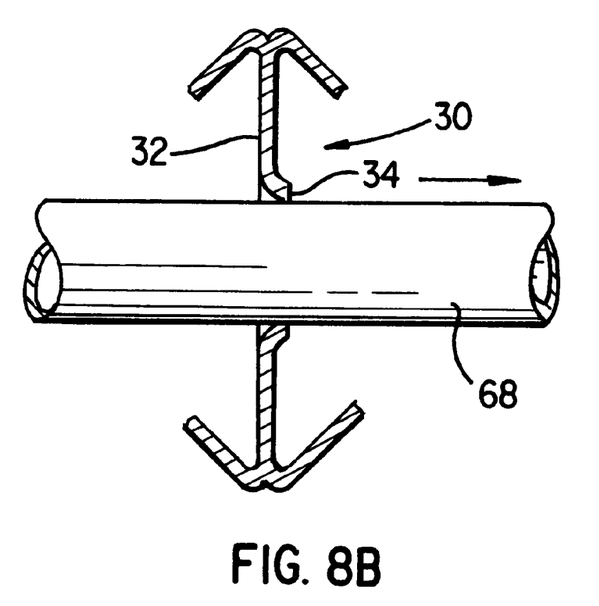

The advantageous maintenance of a small contact pattern between the elastomeric sealing member and both small and large implement traversing the valve can also be understood with reference to FIGS. 8A and 8B. As illustrated in FIG. 8A, elastomeric sealing member 30 is adaptable to provide circumferential contact between a small implement such as a vascular guidewire 66 and the orifice 34 of sealing membrane 32. Such guidewires are quite small in diameter, often being between about 0.070 and 0.005 inches in diameter. Additionally, these intravascular guidewires will often be formed as coils of a high strength biocompatable metal such as stainless steel, platinum, a shape memory alloy such as Nitinol™, or the like. To maintain hemostasis around this irregular coil surface, orifice 34 will often have a nominal diameter which is slightly smaller than the outer diameter of the guidewire. Nonetheless, friction between the elastomeric sealing member 30 and the guidewire is relatively low, in part because only because a limited area of contact between the two surfaces is required. Additionally, fine adjustment of the axial and rotational position of the guidewire may be made without any sliding contact, as membrane 32 can flex quite easily before sliding occurs.

As illustrated in FIG. 8B, once orifice 34 has been radially distended through the application of a vacuum surrounding membrane 32, it will provide hemostasis around relatively large implements such as prosthetic delivery catheter 68. Advantageously, the contact area between the surface of the elastomeric sealing member 30 and the prosthetic catheter remains quite small. This small contact pattern helps avoid any increase in friction despite the great disparity in sizes between the prosthetic delivery catheter and the guidewire.

Figure 9A:
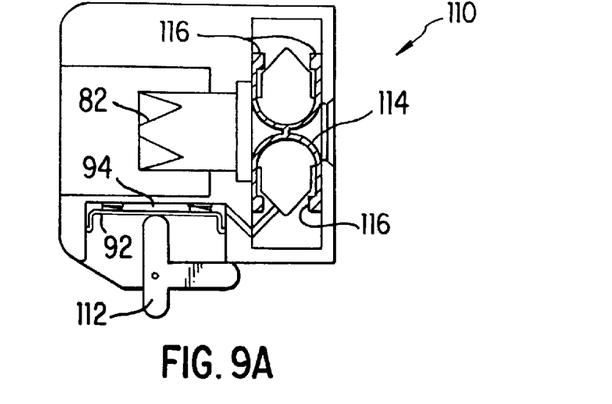
FIGS. 9A–C illustrate a three-position valve having an elastomeric sealing member which defines an inner portion of a torroidal balloon, according to the principles of the present invention.
Figure 9B:
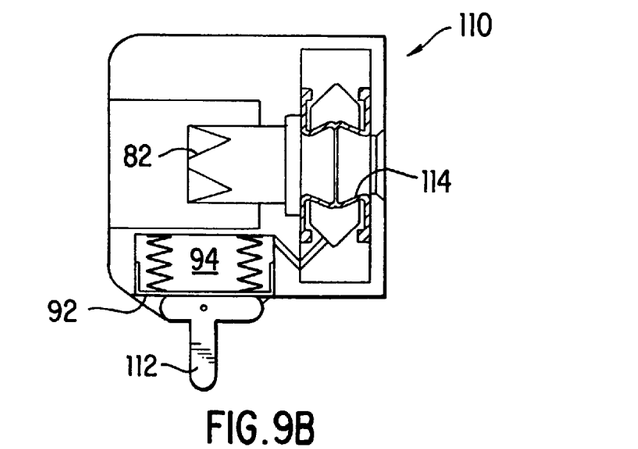
Figure 9C:
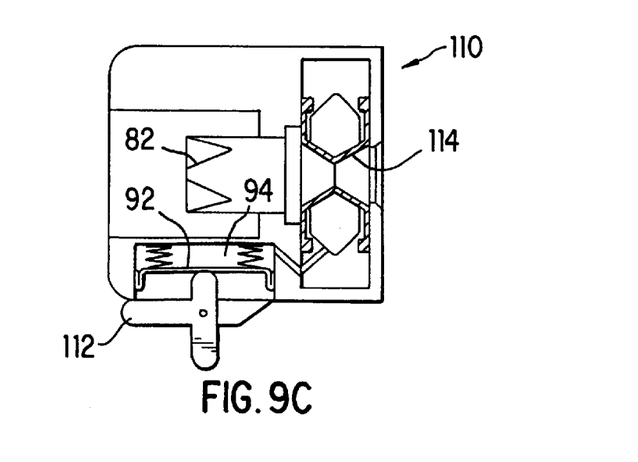

Referring now to FIGS. 9A–C, a three position hemostasis valve 110 has a three position actuator 112. In a first position (as shown in FIG. 9A), the actuator depresses diaphragm 92 to compress vacuum chamber 94. This pressurized the fluid within the torroidal balloon, causing flanged elastomeric sealing member 114 to inflate inwardly, occluding the orifice to a predetermined first size. Flanged sealing member 114 here includes flanges 116 which help restrain the sealing member.

In a second position, (as shown in FIG. 9B), the actuator releases the diaphragm to increase the volume of vacuum chamber 94. the orifice is drawn radially outward to accommodate a larger implement at a predetermined second size. In a third position (as shown in FIG. 9C), the actuator holds the diaphragm in an intermediate position, so that a pressure within the torroidal balloon is between the high pressure of FIG. 9A and the low pressure of FIG. 9B, providing a predetermined third orifice size which is between the first and second orifice sizes.

Optionally, the valve of FIGS. 9A–C may be adapted to seal around a guidewire, an endoluminal prosthesis deployment catheter, and some implement with a cross section between those of the guidewire and the deployment catheter (such as an angiography catheter or an intravenous ultrasound catheter) when the actuator is in the first, second, and third positions, respectively. As before, hemostasis can then be provided by duckbill valve 82, (shown schematically) when no implement traverses the valve. Alternatively, the three actuator positions may provide hemostasis with no traversing implement, a guidewire, and the deployment catheter, while the optional duckbill valve provides redundancy when no implement is inserted. Regardless, the intermediate pressure provided when the actuator is in the third position is optionally roughly equivalent to ambient pressure. Those of skill in the art will recognize that alternative numbers of predetermined orifice sizes, or even infinitely variable orifice sizes within a predetermined range, may instead be provided.

Although the exemplary embodiments of the present invention have been described in some detail, for purposes of clarity of understanding and illustration, a wide variety of modifications and changes to these specific embodiments will be obvious to those of skill in the art. Therefore, the scope of the present invention is limited solely by the appended claims.

What is claimed is:

1. A hemostasis valve for surgical procedures, comprising:
   a rigid body having a passage formed therethrough; and
   an elastomeric sealing member disposed within and sealed to said passage, said sealing member including,
      a first web and a second web each respectively extending from a first circumference and a second circumference of said passage to meet and form an annular space between said first web, said second web and said rigid body, and wherein a volume of said annular space is adjusted by varying pressure, and
      an elastomeric membrane extending from said first web and said second web to define an orifice through which instruments can be inserted, wherein said membrane circumferentially contacts the instruments with a narrow contact band and wherein sizing of said orifice is dependent on a pressure in said annular space.

2. The valve of claim 1, wherein said passage includes an internal surface having an internal groove formed therein.

3. The valve of claim 1, wherein said passage of said body includes a vacuum channel formed therein adjacent said annular space.

4. The valve of claim 1, wherein said elastomeric membrane is a thin, planar membrane.

5. The valve of claim 1, wherein said first web and said second web extend along both sides of said body.

6. The valve of claim 1, wherein said body includes a lumen for connecting said annular space in fluid communication with a pressure varying device.

7. A hemostasis valve system comprising:
   a flexible introducer sheath having a proximal end and a distal end;
   a housing on said proximal end of said sheath; and
   a hemostasis valve disposed in said housing, including;
      an outer body having a passage therethrough, said passage having an internal surface,
      an tubular elastomeric sealing member disposed in said passage, wherein said internal surface of said passage is sealingly fixed between ends of said tubular sealing member such that said internal surface and said sealing member define an annular space therebetween, and wherein a volume of said annular space is adjusted by fluid pressure, and
      a planar elastomeric membrane disposed within said passage and extending from said sealing member across said passage, said elastomeric membrane including an instrument passing orifice, wherein a diameter of said instrument passing orifice is dependent on a pressure in said annular space, and wherein said elastomeric membrane circumferentially contacts instruments inserted through said orifice.

8. The valve system of claim 7, wherein said internal surface includes an internal groove formed therein.

9. The valve system of claim 7, wherein said internal surface includes a vacuum channel formed therein adjacent said annular space.

10. The valve system of claim 7, wherein said ends of said sealing member extend along the sides of said body.

11. A hemostasis valve comprising:
   a valve body having a passage therethrough, said passage having an internal surface;
   an elastomeric sealing member having edges sealingly connected to said internal surface, said sealing member extending from said internal surface such that said internal surface of said passage is disposed between said edges of said sealing member within said passage to define an annular space between said sealing member and said internal surface;
   a planar elastomeric membrane disposed within said passage extending across said passage from said sealing member, said membrane including an instrument passing orifice, wherein said membrane circumferentially contacts instruments inserted through said orifice; and
   an actuator having a vacuum chamber in fluid communication with said annular space, said actuator being moveable between a first position and a second position, wherein when said actuator is in said first position, said orifice is at a first diameter, and when said actuator is in said second position, pressure in said annular space is varied to enlarge said orifice such that said sealing member distends to a second diameter.

12. The valve of claim 11, further comprising a duckbill valve secured within said passage.

13. The valve of claim 11, wherein said actuator is a displacement mechanism which varies a volume of said vacuum chamber.

14. The valve of claim 13, wherein said displacement mechanism is biased to expand said vacuum chamber.

15. A medical device for surgical procedures, the device comprising:
   a guidewire;
   a catheter disposed on the exterior of said guidewire; and
   a hemostasis valve for introducing said guidewire and said catheter into a patient, said valve including,
      a valve body having a rim surrounding an instrument passage hole extending therethrough; and
      a tubular elastomeric body disposed within and sealed to said rim,
      wherein said elastomeric body includes a first web, a second web and a substantially planar elastomeric membrane extending across said instrument passage hole,
      wherein a perimeter of said elastomeric membrane is sealingly fixed to an inner edge of said first web which extends between said perimeter of said elastomeric membrane and a location of a first circumference of said rim, and wherein said perimeter of said elastomeric membrane is sealingly fixed to an inner edge of said second web which extends between said perimeter of said elastomeric membrane and a location of a second circumference of said rim,
      wherein said inner edge of said first web is sealed to said inner edge of said second web,
      wherein an annular space is formed between said first web, said second web, and said rim of said valve body,
      wherein said valve body includes a fluid passage in communication with said annular space, and
      wherein said elastomeric membrane has an instrument passing orifice therethrough,
      such that sizing of said orifice is dependent on a pressure in said annular space which can be adjusted by changing the fluid volume in said annular space through said fluid passage.

16. An introducer valve for surgical procedures, comprising:
   a valve body having a rim surrounding an instrument passage hole extending therethrough; and
   a tubular elastomeric body disposed within and sealed to said rim,
      wherein said elastomeric body includes a first web, a second web and a substantially planar elastomeric membrane extending across said instrument passage hole,
      wherein a perimeter of said elastomeric membrane is sealingly fixed to an inner edge of said first web which extends between said perimeter of said elastomeric membrane and a location of a first circumference of said rim, and wherein said perimeter of said elastomeric membrane is sealingly fixed to an inner edge of said second web which extends between said perimeter of said elastomeric membrane and a location of a second circumference of said rim,
      wherein said inner edge of said first web is sealed to said inner edge of said second web,
      wherein an annular space is formed between said first web, said second web, and said rim of said valve body,
      wherein said valve body includes a fluid passage in communication with said annular space,
      wherein said elastomeric membrane has an instrument passing orifice therethrough,
      such that sizing of said orifice is dependent on a pressure in said annular space which can be adjusted by changing the fluid volume in said annular space through said fluid passage.

17. The valve of claim 16, wherein said valve body includes an internal groove formed in said rim.

18. The valve of claim 17, wherein said internal groove includes a vacuum channel formed therein adjacent to said annular space.

19. The valve of claim 16, further including two endplates adjacent to said valve body.

20. The valve of claim 19, wherein said endplates define said first and said second circumferences.

21. The valve of claim 16, wherein said said first web and said second web extend along each side of said valve body.

22. The valve of claim 16, wherein a maximum diameter of said instrument passing orifice is less than a diameter of said instrument passage hole.

* * * * *